US 8,854,056 B1

United States Patent
Furuhira et al.

(10) Patent No.: US 8,854,056 B1
(45) Date of Patent: Oct. 7, 2014

(54) CAPACITANCE SENSING DEVICES AND METHODS

(71) Applicant: Cypress Semiconductor Corporation, San Jose, CA (US)

(72) Inventors: Akihiro Furuhira, Koshigaya (JP); Ryan Seguine, Seattle, WA (US)

(73) Assignee: Cypress Semiconductor Corporation, San Jose, CA (US)

( * ) Notice: Subject to any disclaimer, the term of this patent is extended or adjusted under 35 U.S.C. 154(b) by 0 days.

(21) Appl. No.: 14/021,521

(22) Filed: Sep. 9, 2013

Related U.S. Application Data

(60) Provisional application No. 61/700,441, filed on Sep. 13, 2012.

(51) Int. Cl.
*G01R 27/26* (2006.01)
*G01N 27/22* (2006.01)

(52) U.S. Cl.
CPC ...................................... *G01N 27/22* (2013.01)
USPC ........... 324/663; 324/658; 324/661; 324/662; 271/265.04; 271/228; 271/227; 347/19

(58) Field of Classification Search
CPC ............. G01R 27/2605; G01R 31/028; G01R 31/312; G01R 31/2831; G01B 7/14; G01B 7/023; G01B 7/087; G01B 7/085; G01N 27/22; G01N 27/221; G01N 27/223; G01D 5/24; G01D 5/2417; G01D 5/2415
USPC .............................. 324/658–690, 519, 750.17
See application file for complete search history.

(56) References Cited

U.S. PATENT DOCUMENTS

| | | | | |
|---|---|---|---|---|
| 3,471,780 A | * | 10/1969 | Beddows | 324/671 |
| 3,519,922 A | * | 7/1970 | Hick et al. | 324/671 |
| 4,610,530 A | * | 9/1986 | Lehmbeck et al. | 399/69 |
| 5,035,415 A | * | 7/1991 | Lee et al. | 271/265.03 |
| 5,168,239 A | * | 12/1992 | Winship | 324/671 |
| 5,198,777 A | * | 3/1993 | Masuda et al. | 324/671 |
| 5,962,861 A | | 10/1999 | Fowler | |
| 6,028,318 A | | 2/2000 | Cornelius | |
| 6,157,793 A | | 12/2000 | Weaver et al. | |
| 6,168,080 B1 | | 1/2001 | Verschuur et al. | |
| 6,229,317 B1 | | 5/2001 | Barchuk | |
| 6,315,473 B1 | | 11/2001 | Slippy | |
| 6,388,452 B1 | | 5/2002 | Picciotto | |
| 6,493,523 B2 | | 12/2002 | Weaver | |
| 6,518,679 B2 | | 2/2003 | Lu et al. | |
| 6,606,928 B2 | * | 8/2003 | Takaishi et al. | 83/210 |
| 6,647,884 B1 | * | 11/2003 | La Vos et al. | 101/485 |

(Continued)

OTHER PUBLICATIONS

International Search Report for International Application No. PCT/US13/59165 dated Feb. 19, 2014; 2 pages.

(Continued)

*Primary Examiner* — Tung X Nguyen
*Assistant Examiner* — Thang Le

(57) ABSTRACT

A system can include an input for receiving objects having a flat shape; a capacitance sensing network comprising a plurality of capacitance sensors positioned to be proximate to the received objects; an operations section coupled to the capacitance sensing network and configured to perform predetermined operations on the objects; and a processor section coupled to receive capacitance sense values from the capacitance sensors and configured to determine the presence and features of received objects, prior to the objects being forwarded to the operations section.

12 Claims, 12 Drawing Sheets

(56) References Cited

U.S. PATENT DOCUMENTS

| | | | |
|---|---|---|---|
| 6,771,913 B2* | 8/2004 | Jeschonek et al. | 399/49 |
| 7,862,689 B2 | 1/2011 | Kawasaki et al. | |
| 8,028,990 B2* | 10/2011 | Miyamoto | 271/265.04 |
| 2001/0040331 A1* | 11/2001 | Forch et al. | 270/58.01 |
| 2002/0096824 A1* | 7/2002 | Forch et al. | 271/226 |
| 2003/0231024 A1 | 12/2003 | Luque | |
| 2005/0017430 A1* | 1/2005 | Takahashi et al. | 271/10.01 |
| 2005/0111869 A1* | 5/2005 | Takami et al. | 399/89 |
| 2011/0081157 A1* | 4/2011 | Mitsuoka et al. | 399/69 |
| 2012/0050216 A1* | 3/2012 | Kremin et al. | 345/174 |
| 2012/0286468 A1* | 11/2012 | Ui | 271/228 |
| 2013/0032993 A1* | 2/2013 | Izumiya et al. | 271/225 |
| 2013/0259505 A1* | 10/2013 | Zaretsky | 399/66 |

OTHER PUBLICATIONS

Lion Precision. Capacitive Sensor Operation and Optimization. Tech Note. Jul. 2006. [Retrieved Jan. 28, 2014.] Retrieved from internet:<URL: http://www.lionprecision.com/tech-library/technotes/tech-pdfs/cap-0020-cap-theory.pdf> entire document.

Madaan et al. Capacitive Sensing Made Easy, Part 1: An Introduction to different Capacitive Sensing Technologies. Cypress Semiconductor. Apr. 2012. [Retrieved Jan. 28, 2014] Retrieved from internet:<URL:http://www.cypress.com/?docID=36129> entire document.

Written Opinion of the International Searching Authority for International Application No. PCT/US13/59165 dated Feb. 19, 2014; 7 pages.

* cited by examiner

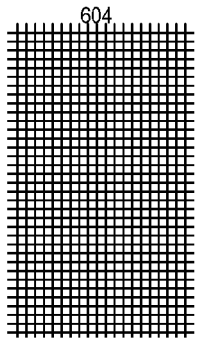 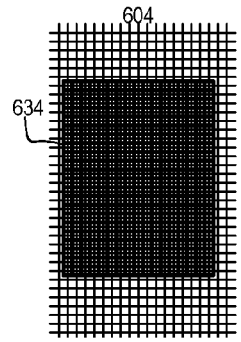 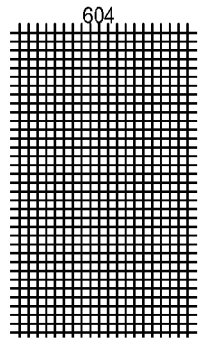 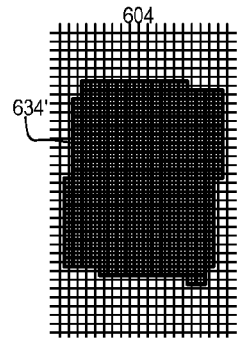
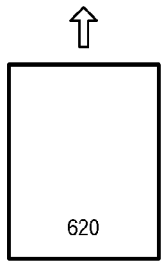   FIG. 6A-1   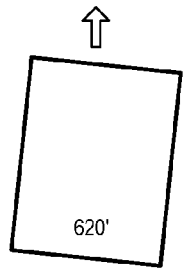   FIG. 6B-1
FIG. 6A-0                FIG. 6B-0
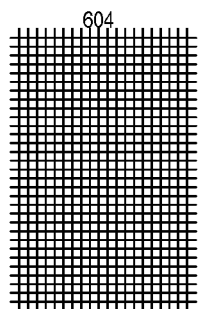 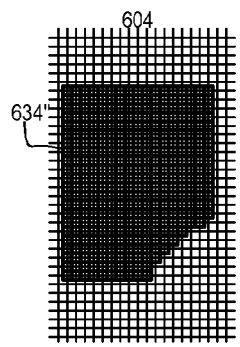
FIG. 6C-1
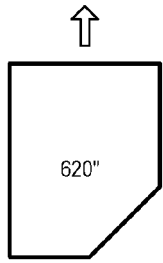
FIG. 6C-0

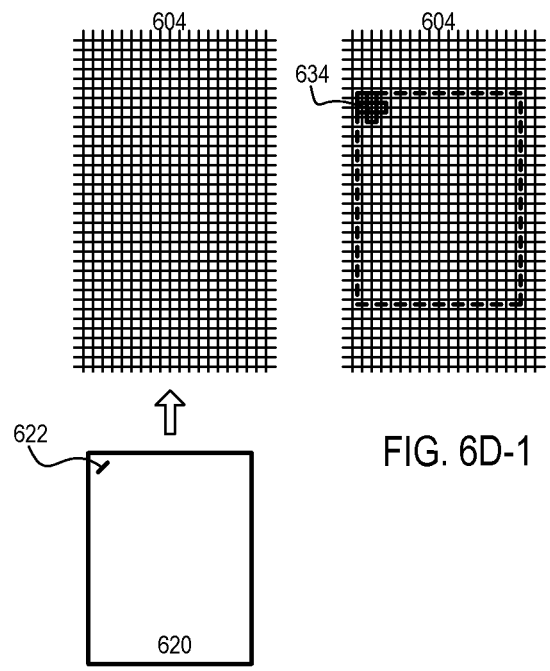
FIG. 6D-1
FIG. 6D-0
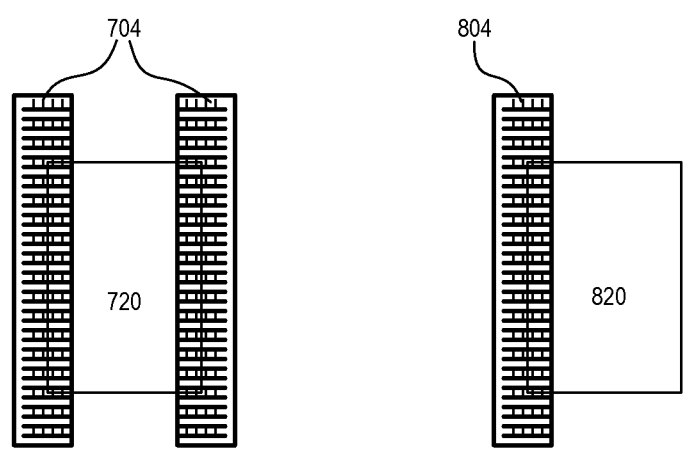
FIG. 7
FIG. 8

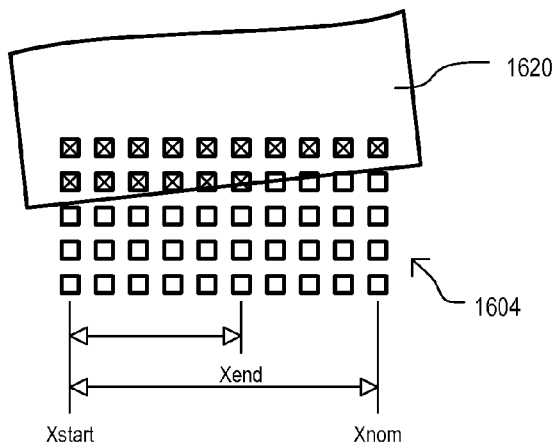
FIG. 16
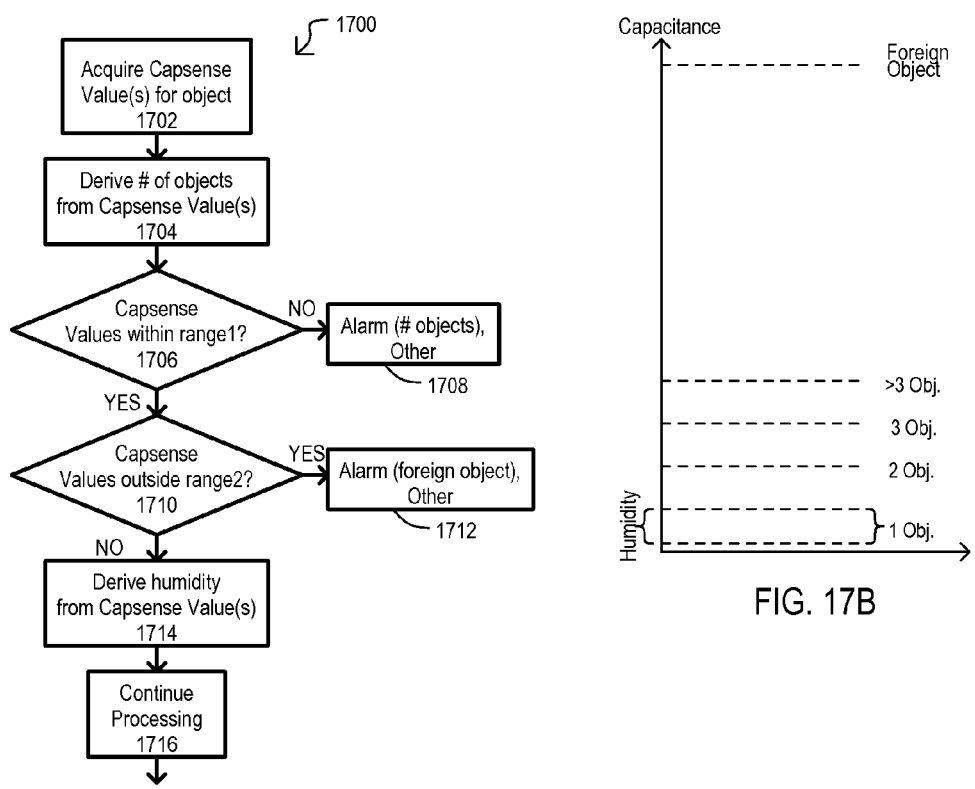
FIG. 17A
FIG. 17B

CAPACITANCE SENSING DEVICES AND METHODS

This application claims the benefit of U.S. provisional patent application Ser. No. 61/700,441 filed on Sep. 13, 2012, the contents of which are incorporated by reference herein.

TECHNICAL FIELD

The present disclosure relates generally to capacitance sensing, and more particularly to capacitance sensing objects to control the processing of the objects.

BACKGROUND

Printing devices can rely on sensing sheets of paper to ensure they are properly processed. Conventional printing systems can utilize light sensors to detect the presence and/or location of a paper in a system. When the paper passes over a sensor, the light path is broken, signaling the presence of the paper.

Conventional printing devices are also known that utilize ultrasound for sensing paper features. In particular, an ultrasound speaker can issue a sound, and according to the attenuation of the signal, a number of sheets of paper can be determined.

BRIEF DESCRIPTION OF THE DRAWINGS

FIGS. 6A-0 to 6D-1 are top plan views showing capacitance sensing of various objects according to embodiments.

FIGS. 7, 8, 9, 10 and 11 show capacitance sensing sections that are smaller than a sensed object, according to embodiments.

FIG. 16 is a diagram showing an alignment detection operation that can be included in embodiments.

FIGS. 17A and 17B are diagrams showing capacitance sense operation according to various embodiments.

DETAILED DESCRIPTION

Various embodiments will now be described that show systems and methods that use capacitance sensing to control the processing of objects. In some embodiments, an array of capacitance sensors can determine the presence of objects, as well as features of such objects, including object size, object alignment relative to other parts of a system, number of objects (in the event objects stack), humidity of the objects (e.g., environment of the object), and/or the presence of foreign objects.

In particular embodiments, objects can be sheets of a material. In a very particular embodiment, an array of capacitance sensors can determine the features of sheets of paper, as the paper is fed into, or from, various sections of a printing device.

Figure 1:
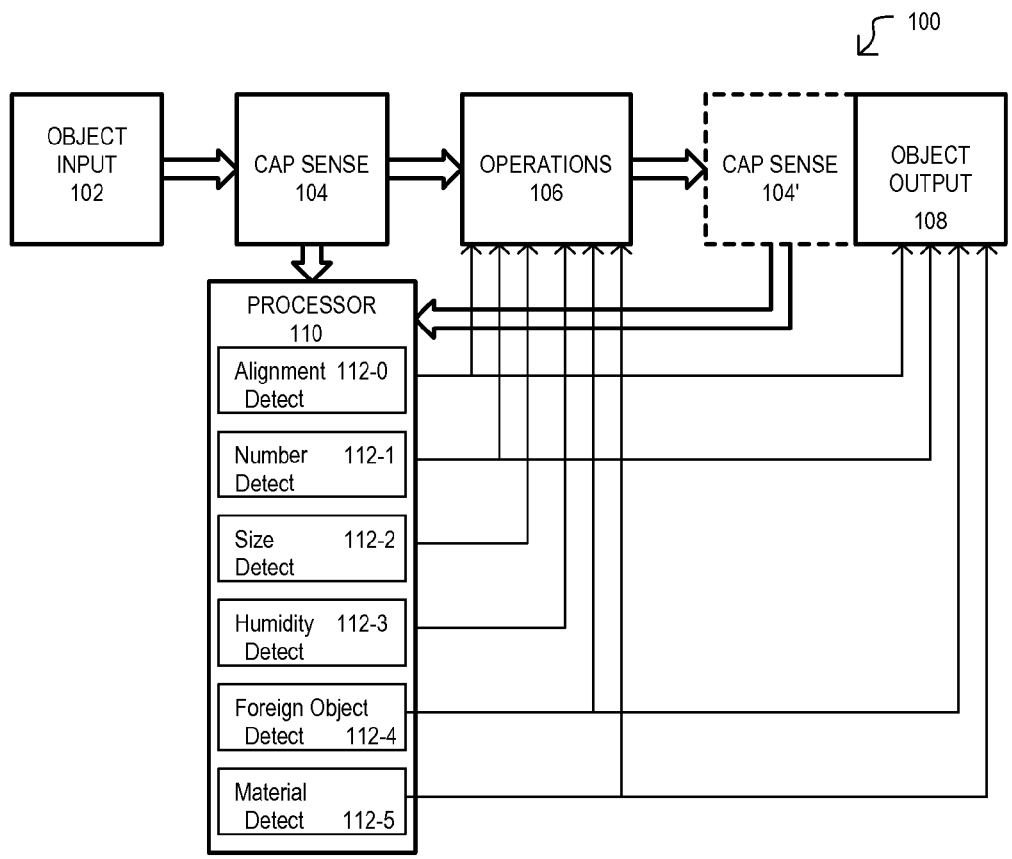
FIG. 1 is a block diagram of a system according to an embodiment.

Referring to FIG. 1, a system 100 according to an embodiment is shown in block schematic diagram. A system 100 can include an object input section 102, a capacitance sense (cap sense) section 104, an operations section 106, an object output 108, and a processing section 110. Optionally, a system 100 can further include a second capacitance sense section 104'. An object input section 102 can provide flat-shaped objects to a capacitance sense section 104. In some embodiments, an object input section 102 can take any suitable form, including a structure as basic as an opening for receiving a flat-shaped object, or can have more complex structures, including those that automatically feed objects from a storage location into a capacitance sense section 104. In very particular embodiments, objects can be flat-shaped objects can have a length, width, and thickness, with a thickness no more than about 1/10th of the smaller length or width.

A capacitance sense section 104 can include an array of capacitance sensors that can sense an area containing a received object (or multiple objects). Such measures of capacitance can be provided by the capacitance sense section 104 itself, or by processing section 110. A capacitance sense section 104 can be larger than a received object, and thus be able to sense the extents of an object in a single scan (a sampling of all sensors). Alternatively, a capacitance sense section 104 can be smaller than a received object, and thus be able to sense the extents of an object with multiple scans, as the object passes adjacent to the array of sensors, or vice versa.

A processing section 110 can receive or generate capacitance values from a capacitance sense section 104, and from such values detect the presence of objects, as well as derive features of objects. Such features can include, but are not limited to: an alignment of the object; the number of objects; the size of an object; the humidity of the object; and the presence of a foreign object (i.e., an object different from those being processed).

An alignment section 112-0 can derive the alignment of an object of an object from capacitance sensor values. Such an alignment can include an orientation of the object in space as compared to a desired orientation. Such orientation can be in a lateral direction (i.e., parallel to a sensor array), as well as a vertical direction (i.e., away from or close to the sensor array).

A number section 112-1 can derive the number of objects. The number of objects can include detecting when more than one object is stacked on top of one another. Further, in some embodiments, such a sensing can determine when objects partially overlap one another, and the extent of any such overlap.

A size section 112-2 can determine a size of an object. A size of an object can include deriving its length, width, perimeter and area, as but a few examples. This can include detecting discontinuities in expected object area (i.e., holes in an object). This can also include detecting shapes of object beyond simple rectangles, ellipses, and circles.

A humidity section 112-3 can determine a humidity of an object. A humidity of an object can include an amount of moisture in an object and/or the humidity of the local processing environment.

A foreign object section 112-4 can detect the presence of a foreign object. A foreign object can be an object other than that which is to be operated on.

An object material section 112-5 can detect the material of which the object is made by referencing the detected capacitance to the capacitance of expected materials. This embodiment may implement additional sensing technologies, including sensing of both mutual and capacitance or optical or ultrasound sensing.

It is understood that in addition to humidity, a processing section 106 can sense any other alteration of an object that varies its capacitance, including but not limited to the presence of coating or the state of a material, as but two examples.

An operations section 106 can perform predetermined operations on an object that are controlled according to one or more of the features derived by processing section 110. Operations performed by an operations section 106 can include any suitable manufacturing operations including but not limited to: printing, painting, imprinting, shaping (cutting, etching, attaching, folding), or coating. Control of an operations section 106 in response to derived features can include, but is not limited to, stopping or preventing the processing of an object, or altering the operation(s) performed on an object.

In very particular embodiments, an operations section 106 can be printing mechanism and objects can be sheets of paper.

An output section 108 can receive can receive processed objects from operations section 106. Like input section 102, output section 108 can take any suitable form, including a structure as simple as an opening for receiving processing objects, to more complex structures, including those that automatically feed processed objects, or perform additional operations on such objects. Operations of an output section 108 can be controlled according to features derived by processing section 110.

In very particular embodiments, an output section 108 can include a collating and/or stapling mechanism for organizing printed sheets of paper.

Optional capacitance sensing section 104' can have a structure like any of those described for 104. However, optional capacitance sensing section 104' can enable features to be derived from objects after they are processed by operations section 106.

Figure 2A:
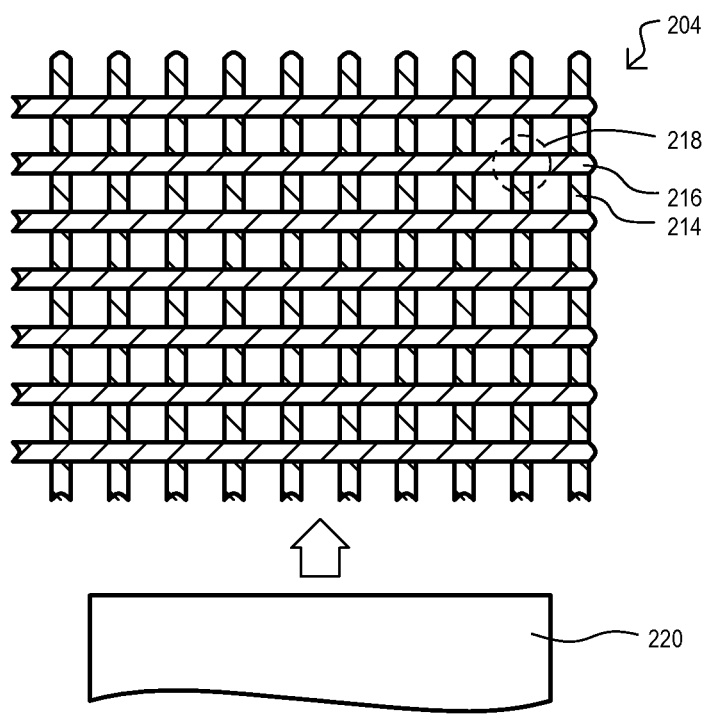
FIGS. 2A and 2B are diagrams showing a capacitance sensing section that can be included in embodiments.
Figure 2B:
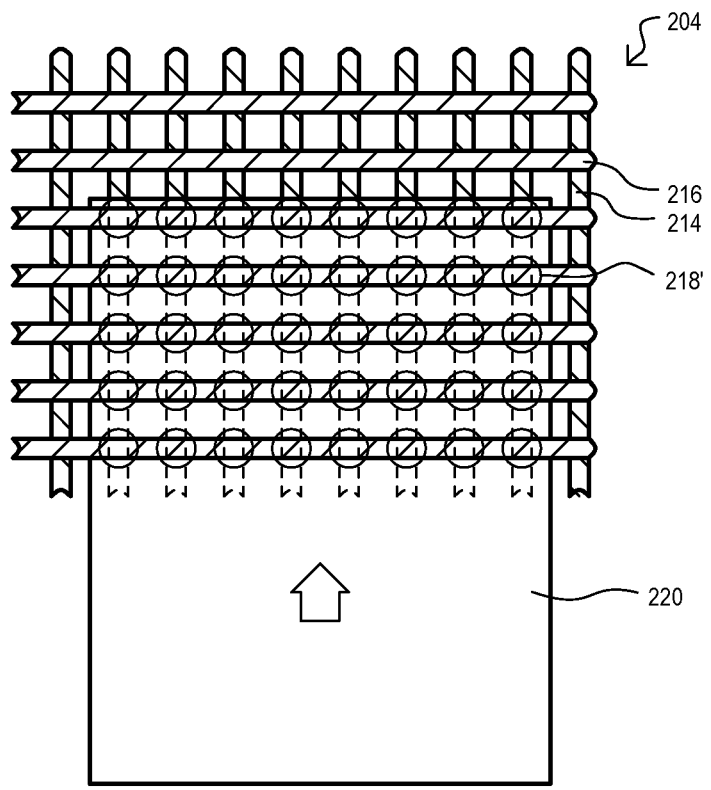

FIGS. 2A and 2B show a capacitance sensing section 204 according to one embodiment. Referring to FIG. 2A, a capacitance sensing section 204 can include a first array of electrodes (one such electrode shown as 214) separated from a second array of electrodes (one such electrode shown as 216). In the embodiment shown, first electrodes 214 can overlap second electrodes 216. A capacitance sensor (one shown as 218) can be conceptualized as being formed at an intersection of the electrodes. An object 220 can be placed between first electrodes 214 and second electrodes 216.

FIG. 2B shows object 220 in a sensing position within capacitance sensing section 204. Object 220 can be placed between first electrodes 214 and second electrodes 216. The presence of the object 220 can result in a variation of the capacitance at sensor locations corresponding to the object (one shown as 218'). As will be described in more detail below, based on such changes in capacitance, various features of an object can be derived. In a very particular embodiment, an object 220 can be a sheet of paper.

While FIGS. 2A and 2B show electrodes having rectangular shapes that are orthogonally oriented with respect to one another, such an arrangement should not be considered limiting. Electrodes can have any suitable shape according to the object to be sensed, as well as the information to be derived. Further, as will also be shown below, a capacitance sensing section 204 can include but one array of electrodes or both arrays of electrodes measured independently (e.g., self-capacitance sensing arrangement).

Figure 3A:
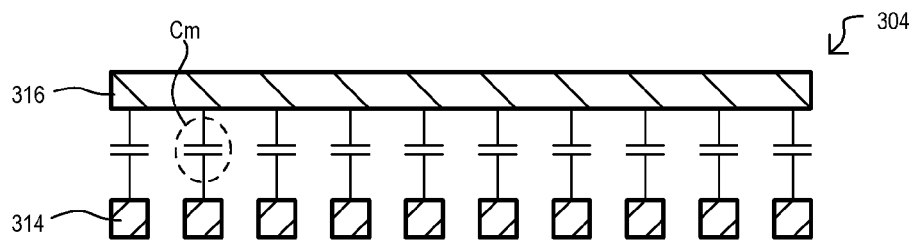
FIGS. 3A to 3G are side cross sectional views of a capacitance sensing array, showing various capacitance sensing operations according to embodiments.

FIGS. 3A to 3G show capacitance sensing operations according to a particular embodiment. FIGS. 3A to 3G show a capacitance sensing section 304 having electrode arrays, like those of FIGS. 2A and 2B, but in a side cross sectional view. Thus, FIG. 3A show first electrodes (one shown as 314) and a second electrode 316 (it being understood that there is an array of such second electrodes). A mutual capacitance can be sensed between first and second electrodes according to any suitable technique.

FIG. 3A shows a capacitance sensing section 304 in the absence of an object. A "baseline" mutual capacitance (one shown as Cm) can exist at intersections of first and second electrodes. Such a baseline mutual capacitance can serve as a reference point. Variations from a baseline capacitance can indicate the proximity of an object.

Figure 3B:
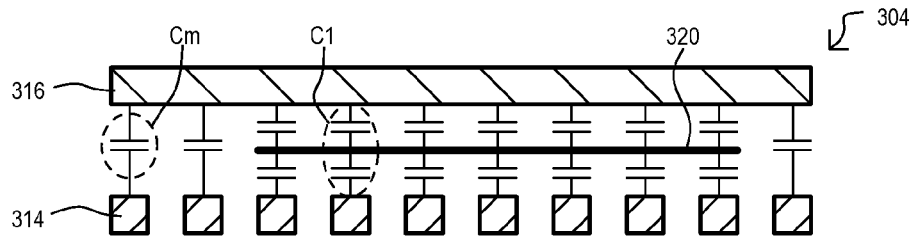

FIG. 3B shows a capacitance sensing section 304 with an object 320 for sensing. The presence of object can result in a change in the mutual capacitance between sensors. Thus, a mutual capacitance a sensor at the location of the object 320 (one shown as C1) can vary from that without the object (one shown as Cm). According to which sensors show a change in capacitance, the extents of an object can be detected. This can enable the derivation of object alignment and/or object size. Further, a capacitance can vary according to humidity, thus according to a sensed capacitance value, a humidity can also be determined. In a very particular embodiment, an object can be paper, and the mutual capacitance can increase with the presence of paper.

Figure 3C:
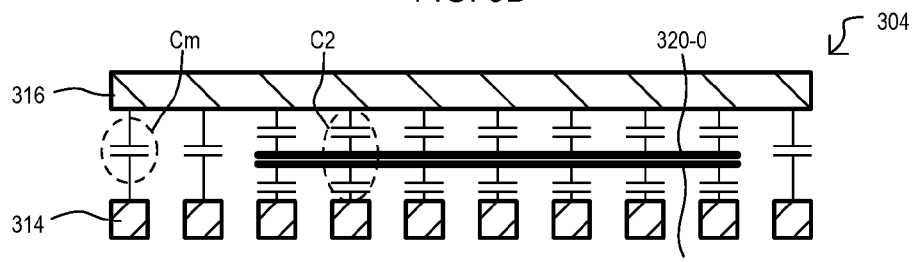

FIG. 3C shows a capacitance sensing section 304 with multiple objects 320-0, 320-1 for sensing. According to some embodiments, as the number of stacked objects increases a sensed capacitance can vary correspondingly. Thus, a capacitance corresponding to multiple objects (one shown as C2) can be different from that corresponding to one object (C1) or no object. In a particular embodiment, a mutual capacitance can increase according to the number of objects. Thus, based on a capacitance value (or sampled values), a number of objects can be detected. In a very particular embodiment, objects can be paper, and the mutual capacitance can increase in an almost linear fashion as the number of sheets is increased.

Figure 3D:
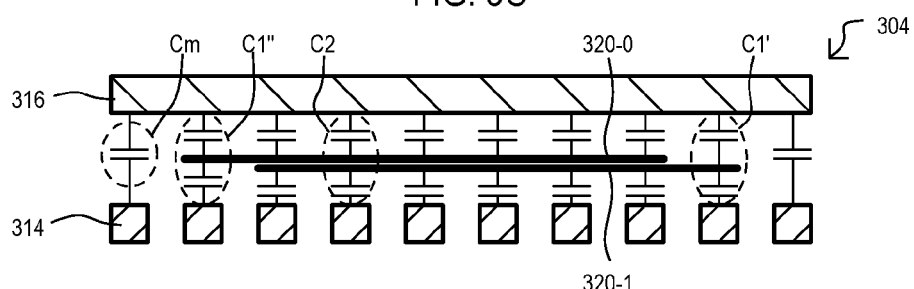

FIG. 3D shows a capacitance sensing section 304 with multiple objects 320-0, 320-1 that only partially overlap one another. Accordingly, some sensor locations can have a capacitance corresponding to multiple objects (one shown as C2), while other locations can show only one object (two shown as C1' and C1"). Thus, based on sensed capacitance values, the extent to which objects overlap one another can be determined.

Figure 3E:
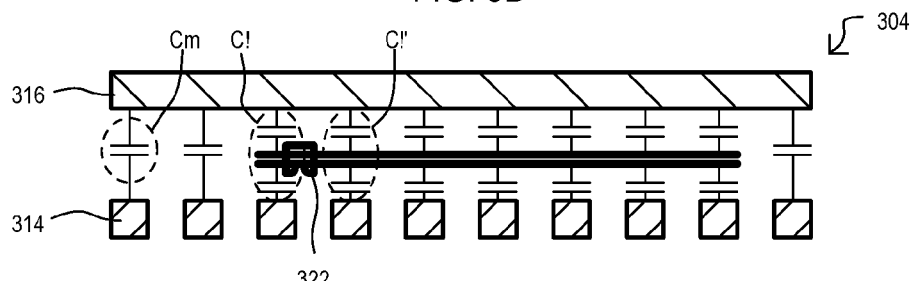

FIG. 3E shows a capacitance sensing section 304 of a foreign object 322. A foreign object 322 can cause a change in capacitance (two shown as C! and C!') that varies from that of standard objects (i.e., objects to be processed or that have already been processed). Thus, the presence of a capacitance reading outside of an expected range can indicate a foreign object. In a very particular embodiment, objects can be paper being input for processing, and a foreign object can include a staple or other metallic item. A staple can result in a substantial increase in capacitance as compared to stacked sheets of paper.

Figure 3F:
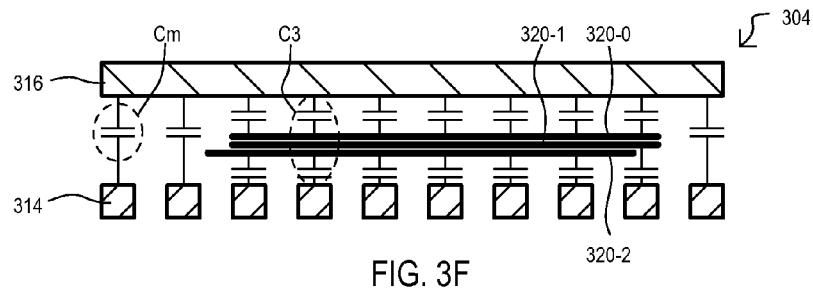

FIG. 3F shows a capacitance sensing section 304 with multiple objects 320-0, 320-1, and 320-2. FIG. 3F shows an arrangement like that of FIG. 3C, but with three objects. It is understood that capacitance C3 can be different than that of C2 (in FIG. 3C), which can be different from that of C1 (in FIG. 3B).

Figure 3G:
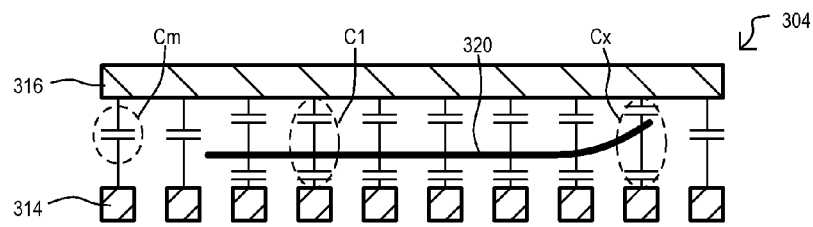

FIG. 3G shows a capacitance sensing section 304 with an object 320 having a feature that causes the object to be closer to one sensor than other portions of the object. A capacitance at the feature location (Cx) can be different from that of other locations (e.g., C1). Thus, capacitance values can be used to detect undesirable deformations, or to confirm irregular shapes in a vertical direction.

While embodiments can utilize any suitable capacitance sensing methods, embodiments with particular capacitance sensing methods will now be described.

Figure 4:
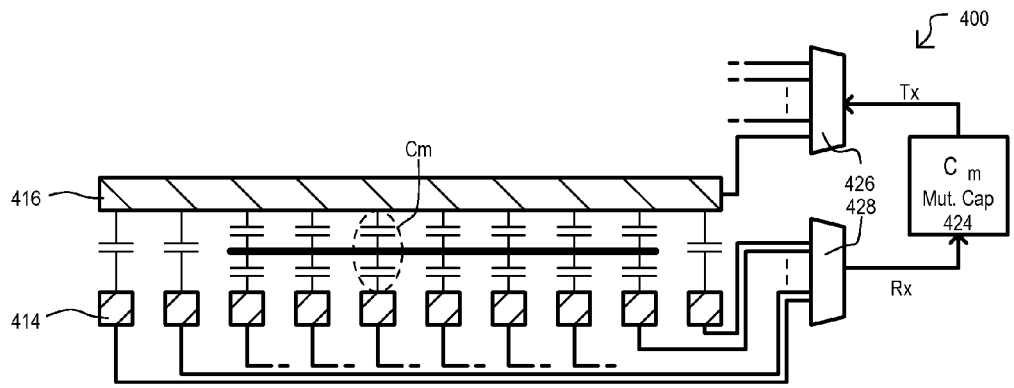
FIG. 4 is a diagram showing mutual capacitance sensing that can be included in embodiments.

FIG. 4 shows a system 400 having a capacitance sensing section like that of FIG. 3 that utilizes mutual capacitance sensing. A system 400 can include a mutual capacitance sensing circuit 424, a transmit de-multiplexer (deMUX) 426, and a receive multiplexer (MUX) 428. Sections 424, 426 and 428 can form part of a capacitance sensing section (e.g., 106) or part of a processing section (e.g., 110).

A mutual capacitance sensing circuit 424 can provide a transmit signal (Tx) which can be driven on one or more transmit electrodes 416 selected by deMUX 426. Transmit signal Tx can induce a signal on receive electrodes 414 that can vary according to a mutual capacitance (e.g., Cm). Receive MUX 428 can selectively connect a receive electrode 414 to mutual capacitance sensing circuit 424 to derive a mutual capacitance value. In one embodiment, a Tx signal can be driven on a transmit electrode, and the receive electrodes can be scanned to derive sense values for a column (or row) of sensors. A next transmit electrode can then be driven to derive values for another row. This can continue until an entire array of values has been acquired.

Figure 5:
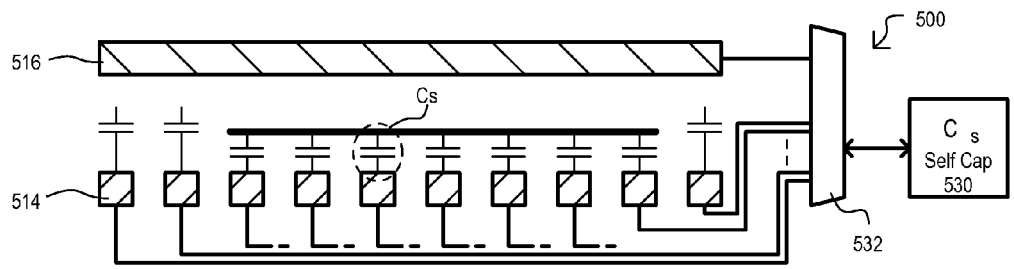
FIG. 5 is a diagram showing self-capacitance sensing that can be included in embodiments.

FIG. 5 shows a system 500 having a capacitance sensing section that utilizes self-capacitance sensing. A system 500 can include a self-capacitance sensing circuit 530 and a sense MUX 532. Sections 530 or 532 can form part of a capacitance sensing section (e.g., 106) or part of a processing section (e.g., 110).

A self-capacitance sensing circuit 530 can measure a self-capacitance of electrodes (one shown as 514), to thereby sense the presence of an object. It is understood that a self-capacitance system could also include a second array of electrodes, as shown in FIG. 4, where such electrodes are formed opposite to the first electrodes 514. These electrodes could also use self-capacitance sensing to determine the presence of an object at a sensor location. In another embodiment, a second axis of self-capacitance sensors (516) may be measured by coupling the array to MUX 532.

As noted above, capacitance sensing sections can sense various features of an object. FIGS. 6A-0 to 6D-1 are diagrams showing various capacitance sense operations for a system that senses a flat-shaped object, such as a sheet of paper. FIGS. 6A-0 to 6D-1 show a capacitance sensing array 604 and corresponding sense pattern 634 resulting from a sense operation.

It is understood that a capacitance sensing array 604 can be one array, or a series of scans from a smaller array taken over time (i.e., as the object passes over the array, or as the array passes over the object). That is, capacitance sensing array 604 can be larger than a sensed object or can be smaller than a sensed object. In the latter case, the capacitance sensing array 604 shown in FIGS. 6A-0 to 6D-1 represent a composite of different scans of the same array.

FIGS. 6A-0 and 6A-1 show a sense operation of an object 620. A sense result 634 can determine various features of the objects as noted herein, or equivalents.

FIGS. 6B-0 and 6B-1 show a sense operation of a misaligned object 620'. It is assumed that an object 620' should have an orientation as in FIGS. 6A-0 and 6A-1. As shown, for a rectangular object, misalignment can result in irregularities at any edges of sensed result 634'.

FIGS. 6C-0 and 6C-1 show a sense operation of a damaged or defective object 620''. It is assumed that an object 620'' should have a shape as in FIG. 6A-0 and 6A-1. As shown, for a defective object, a sensed result 634' can have a smaller area or unexpected discontinuities.

FIGS. 6D-0 and 6D-1 show a sense operation for foreign object 622 present with a scanned object 620. Such a scan operation can have a higher (or lower) capacitance threshold than those used for the object 620 itself. In the particular embodiment shown, the foreign object 622 can be a staple in or on a sheet of paper. Such a stable can result in a localized sense result 634 that surpasses a higher capacitance threshold. FIG. 6D-1 shows the outline of the sheet of paper for reference.

As noted above, a capacitance sense array can be larger than a sensed object, or smaller than a sensed object. FIGS. 7 to 12 show capacitance sense sections according to various embodiments.

FIG. 7 shows a capacitance sense section 704 that can scan opposing edges of an object 720. In the embodiment shown, capacitance sense section 704 can span an entire length of an object 720. In some embodiments, a capacitance sense section 704 can scan for alignment, number of objects, size, humidity, and foreign objects in a portion of the object 720.

FIG. 8 shows a capacitance sense section 804 that can scan one edge of an object 820. As in the case of FIG. 7, capacitance sense section 804 can span an entire length of an object 820. In some embodiments, a capacitance sense section 804 can scan for alignment, number of objects, length (vertical direction in the figure), humidity, and foreign objects in a portion of the object 820.

Figures 9, 10, 11:
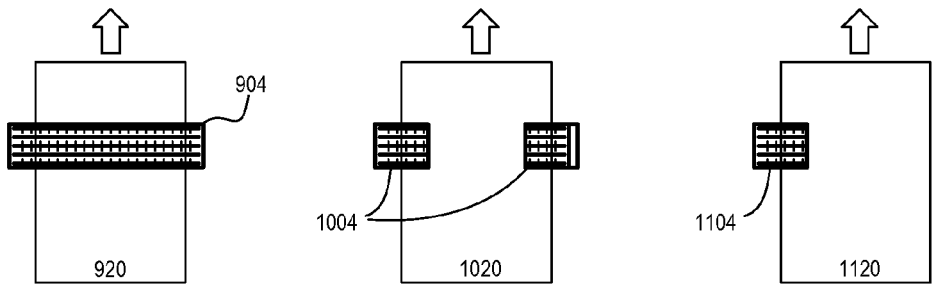

FIG. 9 shows a capacitance sense section 904 that can scan a horizontal strip of an object 920. FIG. 9 shows the intermediate portion of a scan operation. It is understood that the entire object 920 can traverse past the capacitance sense section 904, or vice versa. In some embodiments, a capacitance sense section 804 can scan for alignment, number of objects, size, humidity, foreign objects, or defects in an object 920.

FIG. 10 shows a capacitance sense section 1004 that can scan a horizontal strip at opposing edges of an object 1020. It is understood that the entire object 1020 can traverse past the capacitance sense section 1004, or vice versa. In some embodiments, a capacitance sense section 1004 can scan for alignment, number of objects, size, humidity, or foreign objects in a portion of the object 1020.

FIG. 11 shows a capacitance sense section 1104 that can scan a horizontal strip at one edge of an object 1120. It is understood that the entire object 1120 can traverse past the capacitance sense section 1104, or vice versa. In some embodiments, a capacitance sense section 1104 can scan for alignment, number of objects, size (in one direction), humidity, or foreign objects in a portion of the object 1020.

Figures 12A, 12B, 12C:
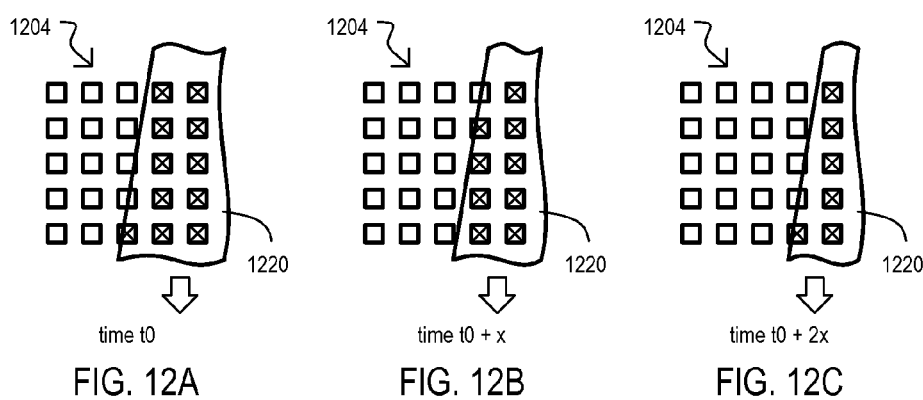
FIGS. 12A to 12C are diagrams showing alignment detection operations that can be included in embodiments.

FIGS. 12A to 12C show an edge scan according to an embodiment. FIGS. 12A to 12C show a capacitance sense array 1204, and a misaligned object 1220 traversing the array over time. Sensors that detect the object are shown with an "X". As shown, edge detection sensors will vary over time as a misaligned object passes over the sensor.

Having described various devices, systems and methods with block and other diagrams, additional methods according to embodiments will now be described in a series of flow diagrams.

Figure 13:
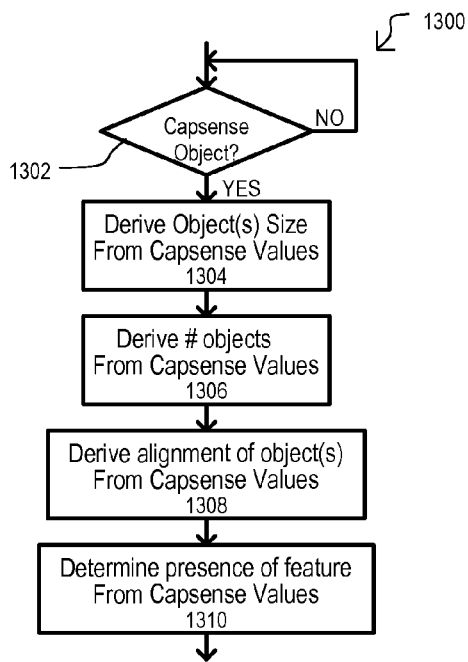
FIG. 13 is a flow diagram of a method according to an embodiment.

FIG. 13 is a flow diagram of a method 1300 according an embodiment. A method 1300 can determine if an object is sensed (1302). Such an action can include sensing a change in capacitance at one or more sensors. If an object is sensed (YES form 1302) a method 1300 can derive various features of the object from the sensed capacitance values. In the embodiment shown, a method 1300 can include deriving object size values 1304 according to any of the embodiments herein, or equivalents.

A method 1300 can also include deriving a number of objects 1306. Such an action can include comparing sensed capacitance values to one or more threshold values corresponding to numbers of objects.

A method 1300 can also include determining an alignment of object(s) 1308. Such an action can include alignment checks as described herein, or equivalents.

A method 1300 can also include determining the presence of other features. Such an action can include scanning for the presence of defects or foreign objects as described herein, or equivalents.

Figures 14A, 14B, 14C:
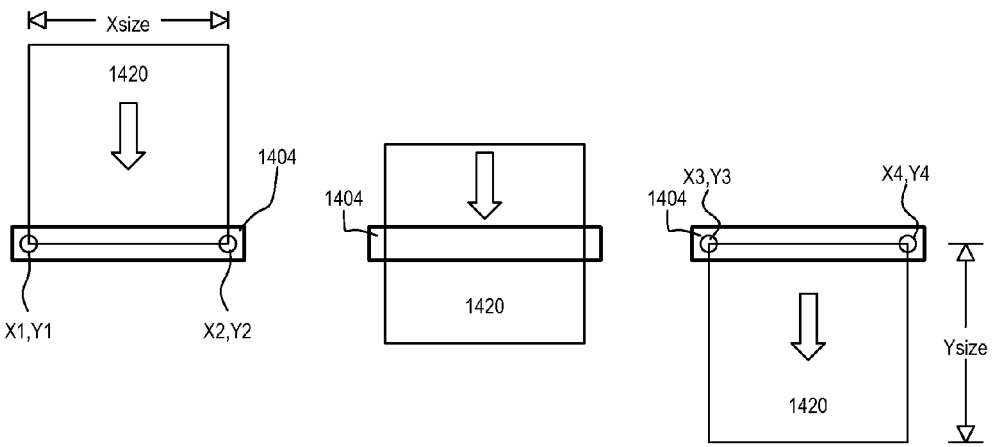
FIGS. 14A to 14C are diagrams showing a capacitance sense operation according to an embodiment.
Figure 15:
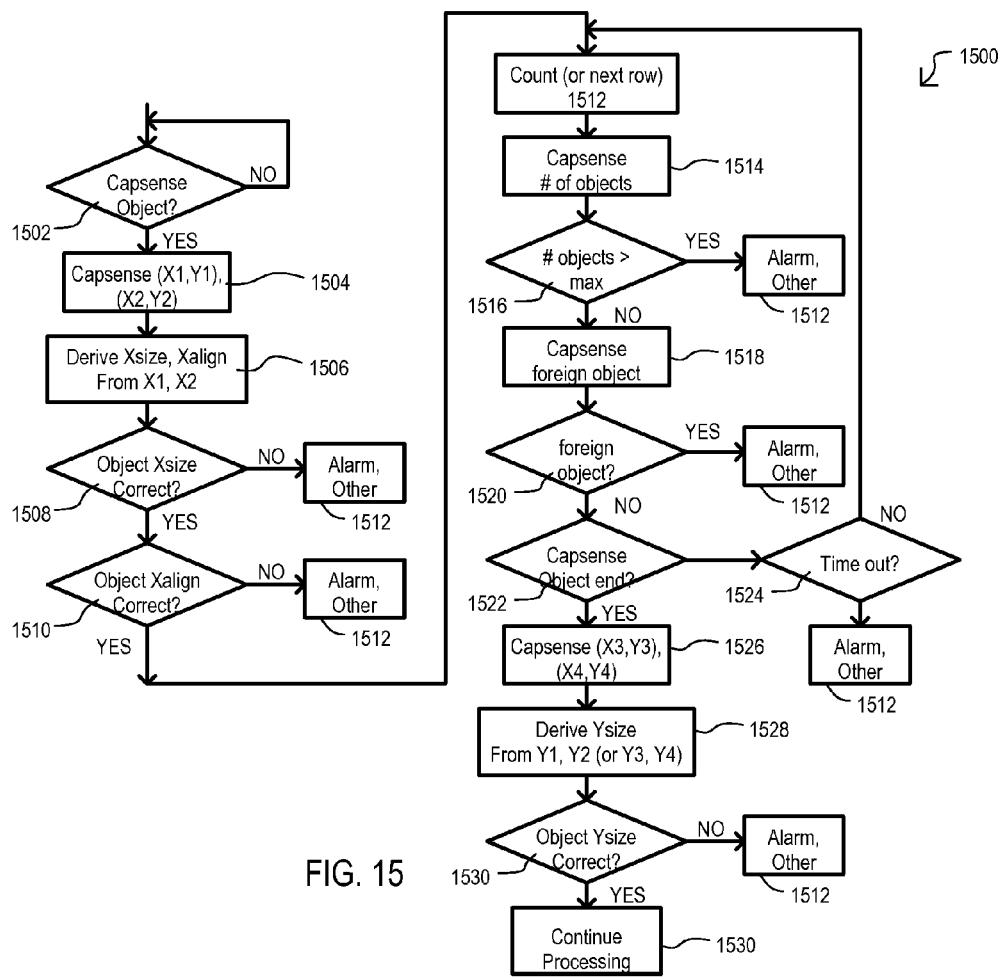
FIG. 15 is a flow diagram of a method corresponding to a sense operation like that of FIGS. 14A to 14C.

FIGS. 14A to 14C show a scan operation according to an embodiment. FIG. 15 shows a method corresponding to the scan shown in FIGS. 14A to 14C. FIGS. 14A to 14C show a capacitance sense section 1404 that can span a strip of an object 1420. An object 1420 can traverse past the capacitance sense section 1404.

Referring to FIG. 15, a method 1500 can include sensing an object with capacitance sense value (1502). It is assumed an object has a flat, rectangular shape. Leading features (e.g., corners) of an object can be sensed (1504). In the embodiment shown, this can include determining X1,Y1 and X2,Y2, as shown in FIG. 14A. It is understood that such points can represent individual sensor values or groups of sensor values (average, local maximum, local minimum, etc.). From leading features, a method 1500 can derive a size and alignment value (1506). In the embodiment shown, a size value can be the size in a lateral direction (Xsize).

If an object size (e.g., Xsize) is not within limits (NO from 1506), predetermined actions can be taken (1512). In the embodiment shown, predetermined actions can include, but are not limited to, issuing an alarm, stopping processing, or adjusting processing. If a size is within limits (YES from 1508), a method 1500 can continue with a series of object checks, including determining if an alignment is within limits (1510). If the alignment is out of range (NO from 1510), predetermined actions can be taken.

A method 1500 can continue scanning the object. Such an action can include allowing a time to pass so that an object can be pushed further past a sensing array, or scanning a next row or sensors (1512).

A method 1500 can then determine a number of objects (1514). In some embodiments, such an action can include comparing one or more sensed capacitance values to one or more thresholds. If the number of objects exceeds some limit (YES from 1516), predetermined actions can be taken (1512).

A method 1500 can check for the presence of foreign objects (1518). In some embodiments, such an action can include comparing sensed capacitance values to one or more thresholds. In some embodiments, such a check can occur as the same time as 1514. If a foreign object is detected (YES from 1520), predetermined actions can be taken (1512).

A method 1500 can then check for an object end (1522). Such an action can include sensing the absence of an object, via capacitance values. If an object end has not been sensed (NO from 1522), a method can check of a time out condition 1524 (i.e., the object has exceeded some size limit, or some other error has occurred). If a time out condition has not occurred (NO from 1524), a method 1500 can return to 1512, scanning more of an object. If a time out condition has occurred (YES from 1524), predetermined actions can be taken (1512).

If an object end has been sensed (YES from 1522), trailing features (e.g., corners) of an object can be sensed (1526). In the embodiment shown, this can include determining X3,Y3 and X4,Y4, as shown in FIG. 14C. Again, such points can represent individual sensor values or groups. With trailing features in combination with leading features, a method 1500 can derive another size value (1528). In the embodiment shown, a size value can be the size in another direction (Ysize).

If this other object size (e.g., Ysize) is not within limits (NO from 1530), predetermined actions can be taken (1512). If a size is within limits (YES from 1530), a method 1500 can continue processing the object (1532) (i.e., and operations section can perform operations on the object). Such an action can include any of the various operations describe herein, or equivalents.

FIG. 16 is a diagram showing an alignment check operation that can be included in particular embodiments. FIG. 16 shows an object 1620 sensed by a capacitance sensor array. In FIG. 16, it is assumed an object 1620 is desired to be aligned with the sensor array. Thus, a misaligned object can have a leading row of sensors (Xstart to Xend) that is less than a nominal value (Xstart to Xnom). Of course, other embodiments can include any other suitable alignment checking technique.

FIGS. 17A and 17B show method according to additional embodiments. FIG. 17A is a flow diagram of a method 1700 according to another embodiment. A method 1700 can include acquiring capacitance sensor values for an object (or objects) (1702). A number of objects can be derived from the sensed capacitance values (1704). If sensed values are not within a first range (NO from 1706), an alarm or other action can be taken (1708), indicating that more than one object has been sensed.

If sensed values are within a first range (YES from 1706), capacitance values can be checked to see if they are outside of another range (1710). If the sensed values are outside of this second range (YES from 1710), an alarm or other action can be taken (1712), indicating that a foreign object has been detected.

If sensed values are within expected ranges, a method 1700 can derive a humidity value for an object based on sensed capacitance values (1714). Processing of the object can then continue (1716).

FIG. 17B is a graph showing one particular example of capacitance sense ranges according to a very particular embodiment. As shown, various thresholds can exist corresponding to number of objects. Further, a humidity range for a single object can also exist. Thus, based on a capacitance value, various numbers of objects can be derived (in the figure, 1, 2, 3 or 4+ objects). In addition, FIG. 17B shows a higher threshold for the detection of foreign objects.

Figure 18A:
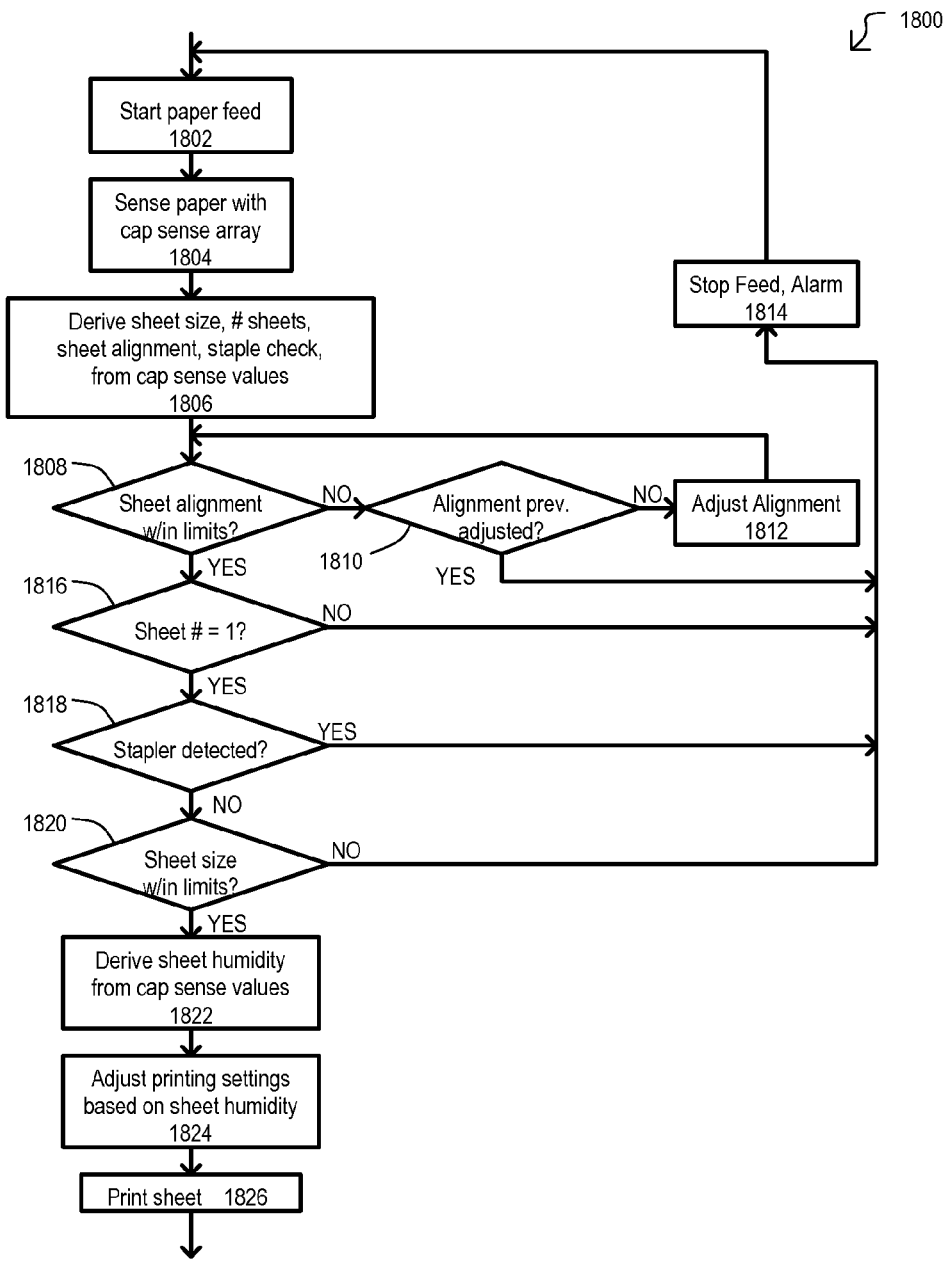
FIGS. 18A and 18B show a flow diagram showing a method of printing according to an embodiment.
Figure 18B:
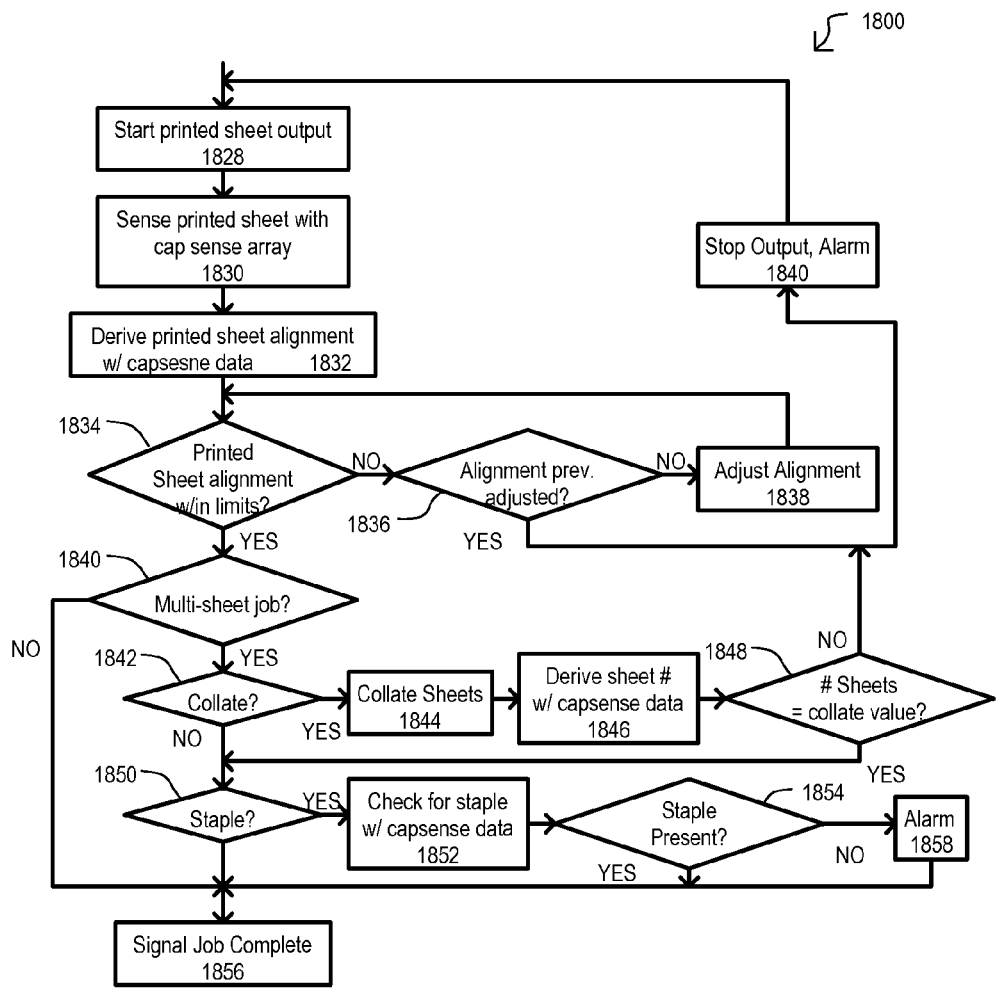

FIGS. 18A and 18B, in combination, are a flow diagram of a method 1800 according another embodiment. Method 1800 can use the capacitance sensing of sheets of paper in a printing operation.

Referring to FIG. 18A, a method 1800 can include starting to feed paper (1802). Paper being fed can be sensed with a capacitance sensing array (1804), as described in the various embodiments herein, or equivalents. Based on capacitance values, a method can derive features of the received paper, including sheet size, number of sheets, sheet alignment, and a staple check (i.e., the unwanted presence of a staple or other foreign object).

If an alignment value is not within limits (NO from 1808), a method can determine if an alignment adjustment operation was previously performed (1810). If an alignment adjustment has not previously been tried (NO from 1810), an alignment adjustment (1812) can be performed, and a method can return to (1808). If an alignment adjustment was previously tried (YES from 1810), the paper feed operation can be stopped and an alarm issued (1814).

If an alignment value is within limits (YES from 1808), a method can determine if the number of sheets is one (1818). If a capacitance value indicates more than one sheet has been detected (NO from 1816), and the paper feed operation can be stopped and an alarm issued (1814).

If the number of sheets has been determined to be one (YES from 1816), a method can determine if a foreign object (e.g., staple) has been detected (1818). If a foreign object is detected (YES from 1818), the paper feed operation can be stopped and an alarm issued (1814).

If no foreign object is detected (NO from 1818), a method can determine if a sheet size (1820). If a sheet size is not within limits (NO from 1820), the print output operation can be stopped and an alarm issued (1840).

If a sheet size is within limits (YES from 1820), a humidity of the paper can be derived from the capacitance values (1822). Print setting can be adjusted based on the derived humidity value (1824), and the sheet can be printed (1826).

Referring to FIG. 18B, a method 1800 can further include starting to output a printed sheet (1828). A printed sheet can be sensed with a capacitance sensing array (1830). Alignment values for the printed sheet can be derived (1832).

If a printed sheet alignment value is not within limits (NO from 1834), a method 1500 follow steps like those described for inputting a sheet for processing (i.e., 1808, 1810, 1812, 1814). A method can then determine if the print operation is a multi-sheet job (1840). If the job is not a multi-sheet job (NO from 1856), the job can be signaled as being complete (1856).

If the job is a multi-sheet job (YES 1856), a method can determine if sheets are to be collated (1842). If collation is to be done, collation can be performed (1844), and the number of sheets of the job can be derived from the capacitance values (1846). If the number of sheets is not the expected value (NO from 1848), the print output operation can be stopped and an alarm issued (1840).

If the number of sheets is the expected value (YES from 1848), a method can then determine if the print operation includes stapling (1850). If stapling is involved (NO from 1850), and the job can be signaled as being complete (1856). If the job includes stapling, a method can check for the stable using capacitance sense values (1852). If the staple is not detected (NO from 1854), an alarm can be issued (1858) and the job can be signaled as being complete (1856). If the staple is detected (YES from 1854), the job can be signaled as being complete (1856).

Figure 19:
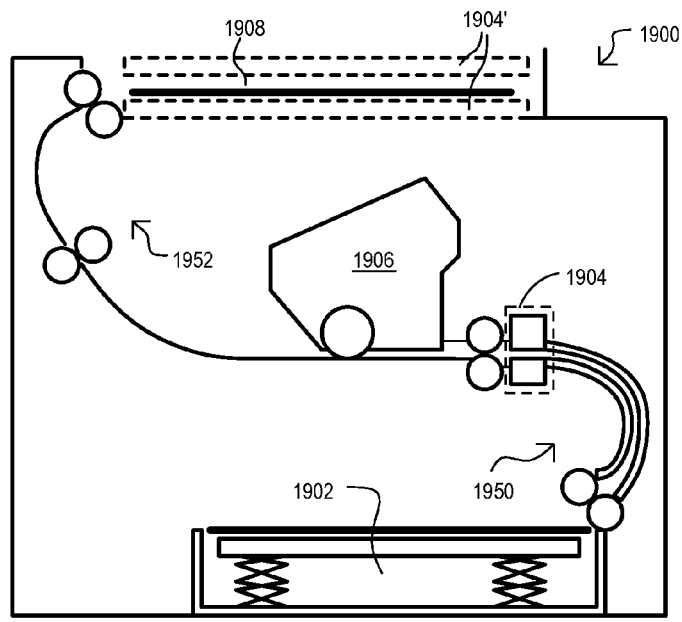
FIGS. 19 and 20 are side cross sectional views of printing devices according to embodiments.

FIG. 19 shows printing device 1900 according to a particular embodiment. A printing device 1900 can include any of: a printer, copier or facsimile machine, as but a few examples. A device 1900 can include an object input 1902, input feed path 1950, first capacitance sense section 1904, an operations section 1906, output feed path 1952, an object output 1908, and optionally, a second capacitance sense section 1904'. An object input 1902 can be a paper feeder that can store a number of sheets. An input feed path 1950 can feed paper to an operations section 1906, and can include guides, rollers, vacuum devices, or any other suitable devices to convey a sheet to the operations section 1906.

A first capacitance sense section 1904 can sense sheets as they are fed to an operations section 1906. A capacitance sense section 1904 can sense various features of a sheet according to any of the embodiments herein. Further, operations of the device can be controlled according to such sensing, including issuing alarms and stopping printing operations. In the embodiment shown, a first capacitance sense section 1904 can be smaller than a sheet, and can scan a sheet as it is conveyed to an operations section. While FIG. 19 shows a first capacitance sense section 1904 proximate the operations section 1906, such a section can be situated at any suitable location along the feed path between the object input 1902 and the operations section 1906.

An operations section 1906 can print on a received sheet. In some embodiments, printing can be varied according to values received from a capacitance sense section 1904. For examples, printing operations can be varied according to a sensed humidity, or varied according to a sensed alignment (i.e., printing can compensate for any misalignment for precision printing).

An output feed path 1952 can feed printed sheets to an object output 1908, and can include guides, rollers, vacuum devices, or any other suitable devices to convey a printed sheet. An object output 1908 can receive printed sheets.

Optional second capacitance sense section 1904' can sense printed sheets as are received. A capacitance sense section 1904 can sense various features of printed sheets according to any of the embodiments herein. Further, operations of the device can be controlled according to such sensing, including issuing alarms, etc. In the embodiment shown, a second capacitance sense section 1904' can be larger than a sheet, and can scan a full sheet within object output 1908.

Figure 20:
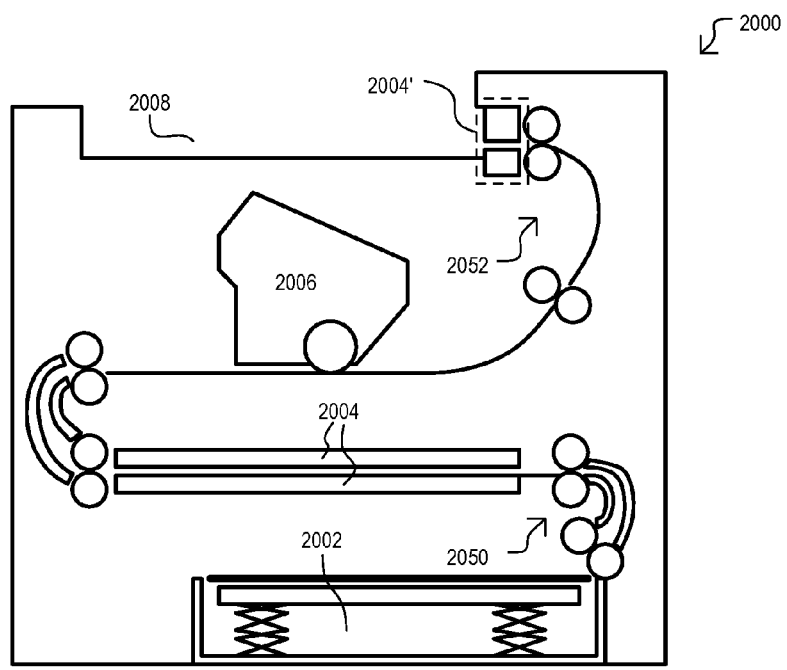

FIG. 20 shows printing device 2000 according to another particular embodiment. A printing device 2000 can include sections like those of FIG. 19, and such like sections are referred to by the same reference character but with the leading digits being "20" instead of "19".

Device 2000 can differ from the of FIG. 19 in that first capacitance sense section 2004 can be larger than a printed sheet, while an optional second capacitance section 2004' can be smaller than a printed sheet. Further, an input feed path It is understood that capacitance sensing as described herein can operate on objects of various sizes and consistencies. In some embodiments, objects can be liquids. In such embodiments, liquid levels flowing through a course, such as a pipe can be detected. Similarly, features of flowing gases can be detected. Other objects can include hands identification cards, or any other suitable object that gives a variation in capacitance.

It should be appreciated that reference throughout this specification to "one embodiment" or "an embodiment" means that a particular feature, structure or characteristic described in connection with the embodiment is included in at least one embodiment of the present invention. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the invention.

Similarly, it should be appreciated that in the foregoing description of exemplary embodiments of the invention, various features of the invention are sometimes grouped together in a single embodiment, figure, or description thereof for the purpose of streamlining the disclosure aiding in the understanding of one or more of the various inventive aspects. This method of disclosure, however, is not to be interpreted as reflecting an intention that the claims require more features than are expressly recited in each claim. Rather, inventive aspects lie in less than all features of a single foregoing disclosed embodiment. Thus, the claims following the detailed description are hereby expressly incorporated into this detailed description, with each claim standing on its own as a separate embodiment of this invention.

What is claimed is:

1. A system, comprising:
an input for receiving objects having a flat shape;
a capacitance sensing network comprising a plurality of capacitance sensors positioned to be proximate to the received objects;
an operations section coupled to the capacitance sensing network and configured to perform operations on the objects; and
a processor section coupled to receive capacitance sense values from the capacitance sensors and configured to determine a presence and features of received objects, prior to the objects being forwarded to the operations section; wherein
the input comprises an input feed path configured to convey received objects over a distance to the operations section, and alter how such objects are conveyed in response to outputs from the capacitance sensing network.

2. The system of claim 1, wherein:
the capacitance sensing network includes at least a first array of a capacitance sensors positioned to be on one side of the object as it is received.

3. The system of claim 2, wherein:
the capacitance sensing network comprises a self-capacitance sensing system configured to measure a self-capacitance of each capacitance sensor.

4. The system of claim 2, wherein:
the capacitance sensing network further includes a second array of a capacitance sensors positioned to be on a side of the received object opposite to that of the first array of capacitance sensors.

5. The system of claim 4, wherein:
the capacitance sensing network comprises a mutual capacitance sensing system configured to measure a mutual capacitance between capacitance sensors of the first array and capacitance sensors of the second array.

6. The system of claim 1, further including:
an output comprising an output feed path configured to convey objects from the operations section, and to alter how such objects are conveyed in response to outputs from the capacitance sense sensing network.

7. The system of claim 1, wherein:
the operations section is configured to adjust an alignment of received objects in response to outputs from the capacitance sense section.

8. The system of claim 1, wherein:
the received object comprises a sheet of a material; and
the operations section is configured to print onto the sheet.

9. The system of claim 8, wherein:
the operations section is configured to adjust printing based on a humidity value derived by the processor section.

10. A system, comprising:
an operations section configured to perform predetermined operations on flat-shaped objects that extend in a planar fashion in a first direction and a second direction perpendicular to the first direction, received from an object input;
a capacitance sensor array disposed proximate to objects processed by the system;
a processing section coupled to the capacitance sensor array, and configured to sense objects and derive processing features therefrom in response to capacitance values from the capacitance sensor array; and
an output configured to collect objects after being operated on by the operations section;
wherein the capacitance sensor array is physically larger than the objects received in the first and second directions.

11. The system of claim 10, wherein:
the processing features are selected from the group of: object size, object alignment, number of objects stacked on top of one another, object humidity, and a presence of a foreign object.

12. The system of claim 10, wherein:
the flat-shaped objects are sheets of a material; and
the operations section is configured to print onto the objects.

* * * * *